United States Patent [19]

Fritze et al.

[11] 4,354,854
[45] Oct. 19, 1982

[54] APPARATUS FOR COLORIMETRICALLY MEASURING TRACES OF GAS

[75] Inventors: Ulrich Fritze; Gerd Janser, both of Cologne; Heinz Herschinger, Leverkusen; Dieter Kitzelmann, Bonn, all of Fed. Rep. of Germany

[73] Assignee: Bayer Aktiengesellschaft, Leverkusen, Fed. Rep. of Germany

[21] Appl. No.: 272,804

[22] Filed: Jun. 11, 1981

[30] Foreign Application Priority Data

Jul. 1, 1980 [DE] Fed. Rep. of Germany ....... 3024847

[51] Int. Cl.³ .................. G01N 31/06; G01N 31/20
[52] U.S. Cl. .................. 23/232 R; 73/863.21; 422/86; 422/88; 422/91
[58] Field of Search ............ 23/232 R; 422/68, 69, 422/83, 86, 88, 91; 261/78 A; 73/863.21

[56] References Cited

U.S. PATENT DOCUMENTS

| | | | |
|---|---|---|---|
| 2,753,753 | 7/1956 | Gardiner | 422/91 X |
| 2,760,922 | 8/1956 | Williams, Jr. | 261/78 A X |
| 2,829,032 | 4/1958 | Barley et al. | 422/86 |
| 3,694,162 | 9/1972 | Kurz et al. | 422/88 |
| 3,912,452 | 10/1975 | Sodickson et al. | 422/91 X |
| 4,299,593 | 11/1981 | Dopp | 422/91 X |

Primary Examiner—Arnold Turk
Attorney, Agent, or Firm—Sprung, Horn, Kramer & Woods

[57] ABSTRACT

Colorimetric measuring arrangement comprising a reaction chamber in which the gas to be measured is absorbed in a reaction liquid and enters into a color reaction. The reaction chamber is in the form of an atomizer in which the reaction liquid is atomized into very fine droplets and thus provides a large surface for the adsorption of gas. The reaction chamber is adjoined by a separation pipe in which the gas phase is re-separated from the reaction liquid. The separation pipe communicates through a liquid guide with an inlet funnel which opens into a micro-throughflow cell. The outlet of the micro-throughflow cell is connected to a siphon. These measures avoid troublesome pulsations in the micro-throughflow cell.

11 Claims, 2 Drawing Figures

APPARATUS FOR COLORIMETRICALLY MEASURING TRACES OF GAS

BACKGROUND OF THE INVENTION

This invention relates to an apparatus for measuring traces of gas and starts out from a colorimetric measuring arrangement preceded by a reaction chamber in which the gas to be measured is absorbed in a reaction liquid and enters into a color reaction.

The object of the apparatus is to detect in good time physiologically harmful gases, for example in laboratories, chemical production plants or in the environment thereof. In the context of the invention, "in good time" means that, within a few seconds of the dangerous gas appearing, even traces of the gas, i.e. fractions of a milliter per cubic meter of ambient air, can be detected and set off an alarm. Another requirement which an apparatus for measuring traces of gas has to satisfy is that, after the appearance of relatively high concentrations of gas, for example of the order of liters per cubic meter, the apparatus should be ready to measure traces of gas again sufficiently quickly, i.e. within a few minutes (a short regeneration time). Not least, an apparatus for measuring traces of gas is required to operate substantially free from maintenance, i.e an interruption for controlling or correcting should only be necessary after prolonged periods of operation, for example 3 weeks or more, which is also when any auxiliary solutions required should be renewed.

In one known method for the sensitive detection of certain extraneous gases, for example in ambient air, the ambient air is passed through a suitable solution with which the gas component to be detected enters into a characteristic color reaction. To enable fluctuating concentrations of extraneous gases to be continuously recorded—which is a basic requirement for any automatic apparatus for measuring traces of gas—the absorption solution has to be continuously renewed. However, if the gas component to be detected is to be absorbed as completely as possible in the absorption solution, steps must be taken to ensure intimate contact between the gas and the liquid. In conventional apparatus, where the gas is bubbled through the liquid by means of glass frits for example, this can only be achieved by prolonged residence of the gas in the liquid.

As a result of this, the gas may not be detected in good time. In addition, the consumption of absorption solution is high. To reduce the consumption of absorption solution, it would be possible to keep the ratio of the continuous stream of absorption solution ($m^3/h$) to the stream of ambient air ($m^3/h$) very low, for example at 1:100. In that case, however, hitherto unsolved problems of flow and absorption would arise in conventional apparatus.

SUMMARY OF THE INVENTION

Accordingly, the object of the invention is to provide a process for measuring traces of gas based on photometric measurement in which a fast response time and high sensitivity are obtained for a low consumption of absorption solution. These requirements are normally conflicting and hitherto have never been simultaneously satisfied.

Starting out from the measuring arrangement described at the beginning, this object is achieved in accordance with the invention by the fact that the reaction chamber is in the form of an atomizer with connections for the gas and the reaction liquid and is adjoined at its lower end by a separation chamber which communicates through a liquid guide with an inlet funnel opening into a micro-throughflow measuring cell, 0.2 to 1 cc in volume, of which the outlet is connected to a siphon. The level of the siphon at the outlet end is advantageously just above the micro-throughflow cell.

Another embodiment of the invention is characterized in that the separation chamber is provided with an inlet pipe through which another auxiliary solution may be added to the reaction liquid after atomization and deposition on the wall of the separation chamber. In this way, the residence time required for the transport of the liquid from the outlet of the atomizer to the micro-throughflow cell may be shortened.

It could not at first be forseen that highly reliable and sufficiently accurate optical measurement could be carried out in a micro measuring cell immediately after the atomizer. Experience had shown that, when a liquid is atomized, gas bubbles are readily introduced and cannot readily be removed again. The appearance of gas bubbles in the micro measuring cell would however make photometric measurement impossible. With the measuring arrangement according to the invention, however, complete separation of the gas phase from the liquid is surprisingly obtained between the atomize and the micro-throughflow cell. In addition, it had been feared that, in view of the small throughflow volumes involved, fluctuations would easily occur, in other words throughflow of liquid through the micro measuring cell would not be uniform, but instead would be subject to pulsations commensurate with the discharge from the atomizer. Pulsations such as these would also seriously affect optical measurement. However, the liquid guide at the end of the separation chamber co-operates with the inlet funnel preceding the micro measuring cell and the following siphon as a stabilization zone so that the fluctuations mentioned are avoided.

The advantages afforded by the invention are essentially due to the fact that a very high proportion of gas may be absorbed in a relatively small quantity of reaction liquid. In this way, high sensitivity is obtained for a very low consumption of reaction liquid. Compared with conventional apparatus, the low consumption of liquid provides for much longer running times. Thus, with continuous operation for example, fresh reaction solution only has to be introduced into the storage vessel every three to four weeks.

By virtue of the small quantities of liquid and the fact that measurement if carried out in the micro-throughflow cell, a very favorable time characteristic is also obtained. In other apparatus of comparable construction, the regeneration time for example after the appearance of a certain concentration is longer by almost one order of magnitude. The fast time characteristic of the apparatus is very important if an alarm is to be set off when a critical value is passed.

The new measuring system operates substantially free from maintenance. By virtue of its compact construction and minimal volume, the arrangement as a whole saves space.

Embodiments of the invention are described in detail in the following with reference to the accompanying drawings, wherein:

DETAILED DESCRIPTION OF THE INVENTION

Figure 1:
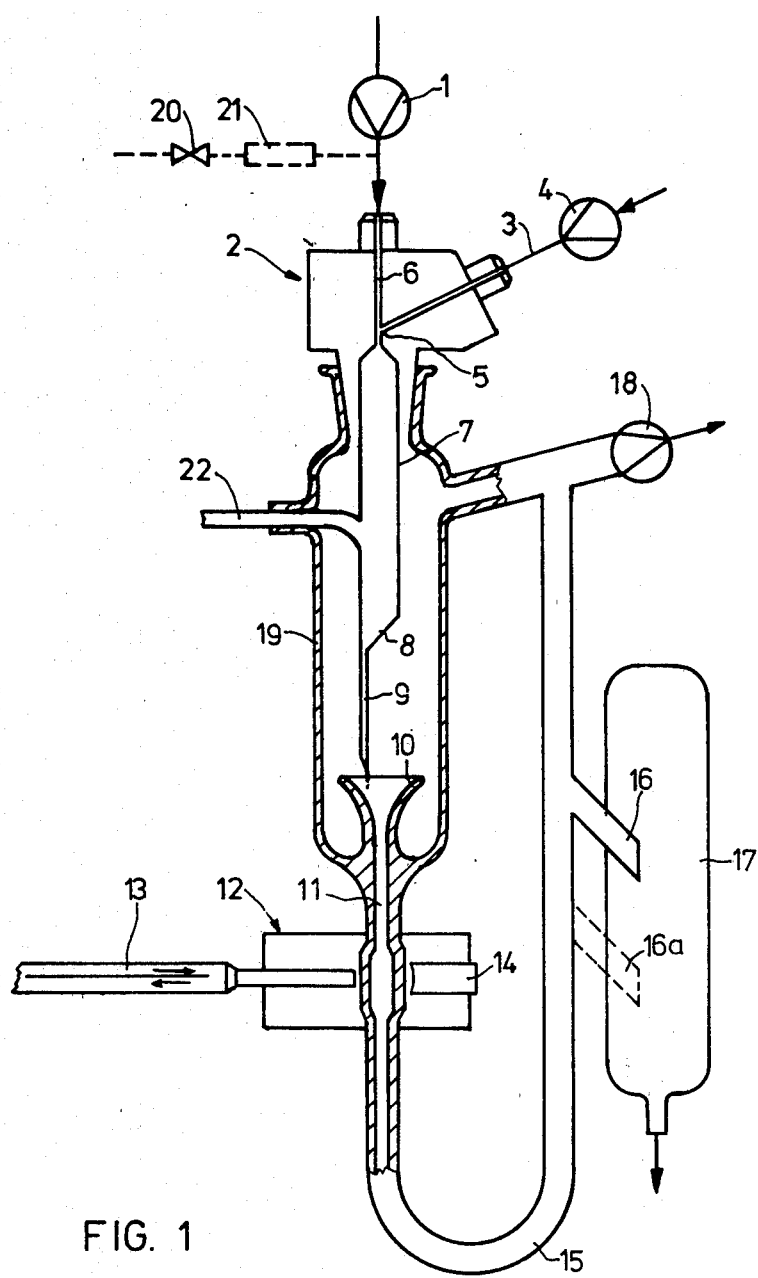
FIG. 1 schematically illustrates the construction of the measuring arrangement.

In the measuring arrangement shown in FIG. 1, the gas mixture (1) to be measured, for example ambient air, is taken into the atomizer 2 by means of a suction pump 18 at a rate of, for example, 500 liters per hour. The reaction solution, for example 20 ml/h, is introduced by means of a metering pump 4 through an inlet 3 in the side of the atomizer 2. The stream of reaction solution passes through the atomizing nozzle 5, for example 0.6 mm in diameter, and is sprayed through the gas flowing past in the narrow bore 6, for example 3.5 mm in diameter. The effect of the pneumatic atomizing operation is to intensively mix the gas with the reaction liquid so that optimal conditions are created for high absorption. At its lower end, the bore 6 widens into a separation pipe 7 with an inlet 22 for another auxiliary solution, for example deionized water which accelerates the transport of the absorption liquid to reduce delays. The liquid collects on the inner wall of the separation pipe 7 and flows downwards in the form of a thin film. In this way, the gas-liquid mixture present in the spray zone 6 is re-separated into a liquid and a gaseous phase. The outflow is accelerated by the gas stream. The lower end 8 of the separation pipe 7 is cut off at an angle of 45° to its axis. The liquid collects at the lowest point of the oblique cut and is delivered via a hydrophilic liquid guide 9, for example a thin glass rod (1 mm in diameter) to the free funnel-like entrance (inlet funnel) 10 of the cell inlet pipe 11. This pipe communicates with a micro-throughflow cell 12, 0.2 to 1 cc in volume. The micro measuring cell 12 is provided with a two-channel light conductor 13. The measuring light admitted through one channel passes through the cell, is reflected at the rear mirror 14, passes back through the cell and is delivered through the other channel of the light conductor 13 to the photoelectric receiver of the colorimeter (not shown). The optical absorption of the liquid flowing through the micro-throughflow cell 12 is measured in this way. The outlet of the micro-throughflow cell 12 is connected to a tubular U-shaped siphon 15. The outlet 16 of the siphon 15 should always be at a higher level than the micro-throughflow cell 12. This ensures that the cell 12 is continuously filled with bubble-free liquid. To obtain a particularly fast response time, the outlet pipe 16 and hence the level of the siphon at the outlet end are situated immediately above the micro-throughflow cell 12 (dashed-line illustration 16a). The liquid flowing out from the outlet 16 is finally collected in a drainage tank 17. The atomizer 2, the separation pipe 7, the liquid guide 9 and the inlet funnel 10 are built into a protective container 19 designed to be evacuated by the pump 18.

The measuring principle is explained once more in the following with reference by way of example to the measurement of traces of phosgene. In this case, the reaction solution consists of a solution of 4-nitrobenzyl pyridine and N-phenyl benzyl amine in phthalic acid diethyl ester. If phosgene is introduced into this solution, an orange-colored compound is formed, having its absorption maximum at 470 nm. The construction of the measuring apparatus is as shown in FIG. 1. The gas to be measured, for example ambient air or chimney exhaust, is drawn through a dust filter (not shown) into the atomizer 2 by the gas pump 18 at a rate of 300 l/h or 50 l/h. At the same time, moist neutral gas (50 l/h) has to be added to compensate for a certain moisture cross sensitivity (approximately 10% of the measured value). To this end, a side pipe with a fine valve 20 and a moistener for the neutral gas is provided on the gas inlet pipe. The neutral gas is air or nitrogen. To neutralize the apparatus, neutral gas is introduced into it instead of the gas to be measured.

The reaction solution mentioned above is delivered to the atomizer 2 by means of the metering pump 4 and sprayed into the gas to be measured flowing past. The effect of the pneumatic mixing operation is to intensively mix the gas with the reaction liquid so that optimal conditions are created for extensive absorption and reaction. Thus, by varying the flow of gas to be measured for the same throughflow of reaction solution, it is possible to alter the measuring range of the analytical apparatus.

The liquid/gas mixture is separated in the separation pipe 7. The measuring solution outflow, which contains the color complex produced by phosgene, flows through the micro-throughflow cell 12 where it is colorimetrically detected. A short regeneration time is guaranteed by constant displacement of the previous measuring solution and the minimization of volume.

Figure 2:
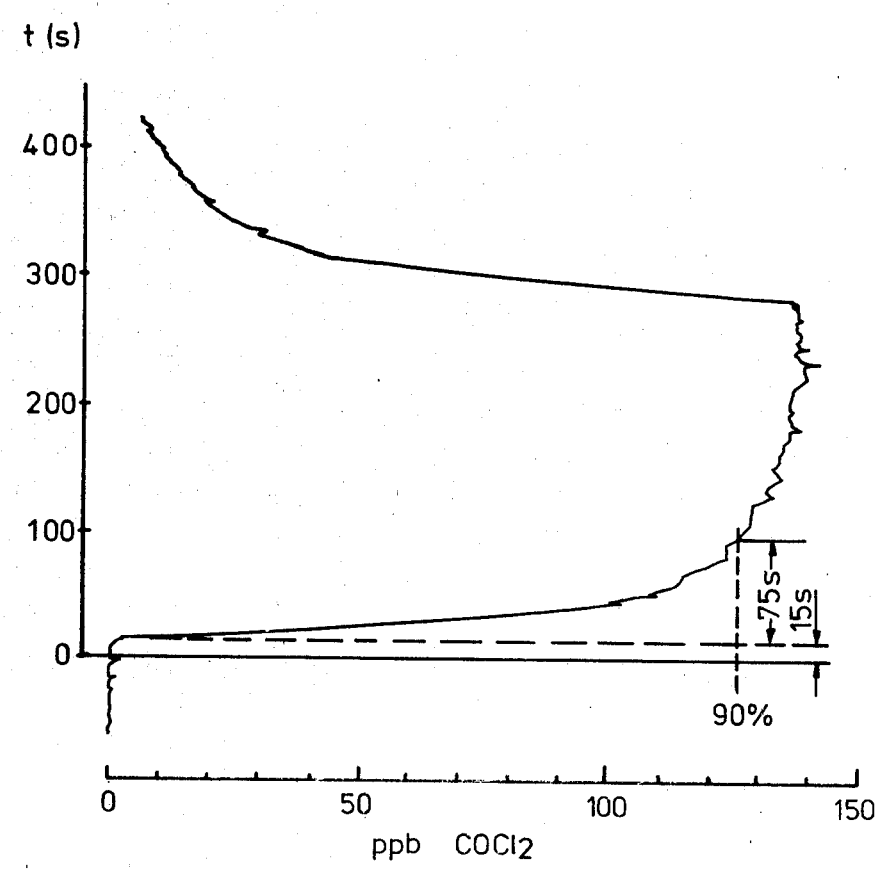
FIG. 2 illustrates the time characteristic of the measuring arrangement with reference, by way of example, to the measurement of phosgene.

FIG. 2 shows the measuring signal (abscissa) as a function of time in seconds (ordinate). At time t=0, ambient air containing 0:15 ppm of phosgene was introduced in the form of pulses into the apparatus. The sensitivity of measurement is excellent. The response time is 15 s and the 90% time 75 s. Systematic measurements have shown that the 90% time of 75 s is largely unaffected by the concentration of the gas to be measured. If, therefore, the MWG (maximum workplace concentration) of 100 ppb is taken as the alarm threshold, the alarm is set off at slightly more than 15 s. This is in line with normal requirements. Accordingly, the apparatus satisfies all the conditions for highly accurate, continuous emission measurement.

In addition to its high precision, sensitivity and specificity, by virtue of its high overload capacity the apparatus is particularly suitable for use where concentration peaks occur.

We claim:

1. In an apparatus for measuring traces of gas, having colorimetric measuring means preceded by means forming a reaction chamber in which the gas to be measured is absorbed in a reaction liquid for entering into a color reaction, the improvement wherein the colorimetric measuring means comprises a micro-flow cuvette and the means forming the reaction chamber comprises an atomizer with connections for the gas and the reaction liquid, a separation pipe adjoining the atomizer at the lower end thereof and means for stabilizing the flow of the reaction liquid with the absorbed gas through the cuvette comprising a liquid guide at the lower end of the separation pipe comprising a thin hydrophilic rod, an inlet funnel separated from and in liquid communication with said rod and discharging into the cuvette, and a siphon connected to the output of the cuvette and having its outlet at a higher level than the level of the cuvette.

2. An apparatus according to claim 1, wherein the level of the siphon at the outlet end thereof is situated immediately above the micro-flow cuvette.

3. An apparatus according to claim 1 or 2, wherein the separation pipe has an inlet pipe for an auxiliary solution to be added to the reaction liquid after it has been atomized and deposited on the wall of the separation pipe.

4. An apparatus according to claim 1, further comprising a protective casing around the atomizer, the separation pipe, the liquid guide and the inlet funnel are built into a protective container.

5. In a method for the colorimetric measuring of traces of gas wherein the gas to be measured is absorbed in a reaction liquid and enters into a color reaction, the improvement comprising the steps of:

absorbing a gas in a reaction liquid by atomizing the liquid with the gas;

passing the liquid and absorbed gas downwardly through a separation pipe as a thin film on the wall thereof;

communicating the thin film downwardly from the pipe into a micro-flow cuvette while stabilizing the flow of the reaction liquid with the absorbed gas through the cuvette by passing the reaction liquid and absorbed gas from the pipe along a thin hydrophilic rod-like liquid guide, thereafter through a funnel separated from said guide and then into the cuvette, siphoning off the reaction liquid with the absorbed gas from the outlet of the cuvette and outletting the siphoned off liquid above the level of the cuvette.

6. The method according to claim 5, wherein the outlet for the siphoned off liquid is disposed immediately above the level of the cuvette.

7. The method according to claim 5, further comprising adding an additional solution to the thin film on the wall of the separation pipe.

8. An apparatus according to claim 1, wherein the downward end of the rod is cut at an oblique angle.

9. An apparatus according to claim 1, wherein the cuvette has a volume of 0.2 to 1 cc.

10. The method according to claim 5, wherein the downward end of the rod-like guide is cut at an oblique angle.

11. The method according to claim 5, wherein the cuvette has a volume of 0.2 to 1 cc.

* * * * *